United States Patent
Shih (10) Patent No.: US 10,925,921 B2
(45) Date of Patent: Feb. 23, 2021

(54) FERMENTED PENNISETUM EXTRACT

(71) Applicant: Sagittarius Life Science Corp., Taipei (TW)

(72) Inventor: Ming-Chi Shih, Taipei (TW)

(73) Assignee: Sagittarius Life Science Corp., Taipei (TW)

( * ) Notice: Subject to any disclaimer, the term of this patent is extended or adjusted under 35 U.S.C. 154(b) by 0 days.

(21) Appl. No.: 16/237,105

(22) Filed: Dec. 31, 2018

(65) Prior Publication Data

US 2019/0134139 A1 May 9, 2019

Related U.S. Application Data

(62) Division of application No. 15/213,806, filed on Jul. 19, 2016, now Pat. No. 10,213,472.

(51) Int. Cl.
| | |
|---|---|
| *A61K 36/899* | (2006.01) |
| *A61K 45/06* | (2006.01) |
| *C12P 1/02* | (2006.01) |
| *A23L 33/105* | (2016.01) |

(52) U.S. Cl.
CPC .......... *A61K 36/899* (2013.01); *A23L 33/105* (2016.08); *A61K 45/06* (2013.01); *C12P 1/02* (2013.01); *A23V 2002/00* (2013.01); *A61K 2236/19* (2013.01); *A61K 2236/333* (2013.01)

(58) Field of Classification Search
CPC ......... C11C 3/003; C11C 3/04; C07K 14/415; C07K 14/43518; C07K 14/43563; C07K 14/43581; C07K 14/43586; C07K 14/43595; C07K 14/75; C07K 17/10; C07K 2319/20; C10G 2/00; C10G 2/30; C10L 1/026; C10L 2200/0476; C10L 2290/544; C10L 5/44; C10L 1/02; C10L 2200/0469; C10L 2200/0492; C10L 2270/026; C10L 2290/02; C10L 2290/04; C10L 2290/06; C10L 2290/26; C10L 2290/28; C10L 2290/30; C10L 2290/42; C10L 2290/24; C11B 1/10; C11B 3/001; C11B 3/006; C11B 3/10; C11B 3/14; C11B 7/0075; C11B 1/00; C11B 1/04; C11B 7/0008; C12N 15/8218; C12N 15/8247; C12N 9/1051; C12N 15/8257; C12N 15/52; C12N 9/004; C12N 9/0042; C12N 15/8245; C12N 15/8246; C12N 15/8261; C12N 15/8297; C12P 7/6463; C12P 1/02; C12P 7/04; C12P 7/24; C12P 7/6409; Y02E 50/30; Y02E 50/343; Y02E 20/16; Y02E 20/18; Y02E 50/10; Y02E 50/13; Y02E 50/14; Y02E 50/17; Y02E 50/32; C01B 2203/1211; C01B 32/40; C01B 3/22; C07C 67/48; C07C 29/136; C10B 53/02; C10J 2300/0906; C10J 2300/0916; C10J 2300/1659; C10J 2300/1846; C10J 3/82; C12Y 204/01101; C12Y 106/02002; C12Y 106/02004; A23K 10/30; A23K 20/153; A23L 33/105; A23V 2002/00; A61K 2236/19; A61K 2236/333; A61K 31/717; A61K 36/899; A61K 38/1767; A61K 45/06; B01J 19/127; B01J 2219/1203; C08B 15/005; C08B 15/06; C08L 89/00; C12R 1/645; Y02A 40/146; A61P 35/00; A61P 35/04

See application file for complete search history.

(56) References Cited

U.S. PATENT DOCUMENTS

| | | | | |
|---|---|---|---|---|
| 2008/0138828 A1* | 6/2008 | Valluri | .................... | A01H 3/00 435/7.1 |
| 2010/0323041 A1* | 12/2010 | Cyr | ........................ | A61K 36/15 424/732 |

FOREIGN PATENT DOCUMENTS

| | | |
|---|---|---|
| TW | 201136600 A | 11/2011 |
| TW | 201336504 A | 9/2013 |

OTHER PUBLICATIONS

Mathew et al "Determination of In Vitro Free Radical Scavenging and Antiproliferative Effect of *Pennisetum alopecuroides* on Cultured A549 Human Lung Cancer Cells" Ancient Science of Life vol. 34, pp. 175-178, 2015.
Wong et al "Development of Fermentation in Traditional Chinese Medicine" World Science Technology vol. 12, pp. 437-441, 2010.
Office Action Issued in Chinese Patent Application No. 201710073373.5 dated Mar. 11, 2020.

\* cited by examiner

*Primary Examiner* — Deborah K Ware
(74) *Attorney, Agent, or Firm* — Cesari & McKenna, LLP (57) ABSTRACT

The invention provides a fermented *Pennisetum* extract, which has an advantageous effect in treating and preventing a cancer without toxicity to normal cells. The invention also provides a process of preparing the fermented *Pennisetum* extract and the application of the fermented *Pennisetum* extract in the treatment or prevention of a cancer.

16 Claims, 11 Drawing Sheets

Fig. 1 (A)
Biotransformation of ZG5235, ZG5236 and ZG5237
Before

Fig. 1 (B)
After

* compare with control
§ compare with tumor group

FERMENTED PENNISETUM EXTRACT

CROSS-REFERENCE TO RELATED APPLICATION

The present application is a division of U.S. application Ser. No. 15/213,806, filed Jul. 19, 2016. The content of the prior application is hereby incorporated by reference in its entirety.

BACKGROUND

Field of the Invention

The invention relates to an extract of fermented *Pennisetum* and its application in treatment or prevention of a cancer. Particularly, the invention provides a fermented *Pennisetum* extract comprising compounds exhibiting at least the two peaks at specific retention times measured by High Performance Liquid Chromatography (HPLC).

Background Information

Cancer remains one of the major causes of death around the world. Medicinal herbs have been traditionally used for a variety of purposes, particularly to prevent and treat a variety of diseases including cancer. Particularly, lung cancer can be histologically subclassified into squamous cell carcinoma, small cell carcinoma, adenocarcinoma, large cell carcinoma, carcinoid tumor, mesothelioma, etc. Carcinoma, especially small cell carcinoma of the lung, has the ability to metastasize early and widely, initially to lymph nodes, then to brain, bone, liver, and skin.

It may be noted that plants are considered a valuable resource for the discovery and development of novel, naturally derived agents to treat cancer. *Pennisetum* is a widespread genus of plants in the grass family, native to tropical and warm temperate regions of the world. It has low water and nutrient requirements, and therefore can make use of otherwise uncultivated lands. TW 201136600 and TW 201336504 provide anti-cancer *Pennisetum alopecuroides* (L.) extracts which are obtained by acid solution, basic solution and solvent treatments, respectively; the resulting solutions are treated with cell disruption, filtration and column chromatography. However, there is still a need to develop a *Pennisetum* extract with advantageous anti-cancer effect.

SUMMARY

The invention provides a process for preparing a fermented *Pennisetum* extract, comprising the following steps: (a) culturing *Pennisetum* solution with *Aspergillus niger* for a biotransformation; (b) collecting the resulting cultured solution and then extracting the extract with an organic solvent; and (c) analyzing the extract by High Performance Liquid Chromatography (HPLC) at 330 nm. In one embodiment, the *Pennisetum* solution is 40% (v/v) *Pennisetum alopecuroides* (L.) in ethanol. In one embodiment, the organic solvent of step (b) is an alcohol. In one embodiment, after step (b), the process comprisesa further step (b1) of concentrating the extract to a concentrated extract can be performed.

The invention provides a fermented *Pennisetum* extract, comprising a compound ZG5236 having a chromatograph having at least a peak at retention times of 17.18 to 17.98 minutes. Preferably, the peak is at retention time of about 17.53 minutes in the HPLC. In some embodiments, the extract comprises a compound ZG5235 having a chromatograph having the peak at retention times of: 16.20 to 17.10 minutes, preferably, 16.63 minutes; and/or a compound ZG5237 having a chromatograph having the peak at retention times of: 19.00 to 19.36 minutes.

In some embodiments, the *Pennisetum* mentioned herein is selected from the group consisting of: *Pennisetum alopecuroides* (L.), *Pennisetum clandestinum*, *Pennisetum polystachion* (L.), *Pennisetum purpureum* and *Pennisetum setosum*. Preferably, the *Pennisetum* is *Pennisetum alopecuroides* (L.) or *Pennisetum purpureum*.

In one embodiment, the fermented *Pennisetum* extract comprises compounds ZG5235, ZG5236 and ZG5237. In another embodiment, the amount of ZG5236 after biotransformation is higher than that before the transformation, while the amounts of ZG5235 and ZG5237 after biotransformation are lower than those before the transformation.

The invention also provides a composition comprising the fermented *Pennisetum* extract.

The invention further provides a method for treating a cancer and/or invasion and metastasis of cancer in a subject in need thereof, comprising administering to the subject an effective amount of the *Pennisetum* extract of the invention.

BRIEF DESCRIPTION OF THE DRAWINGS

The description below refers to the accompanying drawings, of which:

FIGS. 1(A) and (B) show the HPLC spectra of *Pennisetum alopecuroides* (L.) solution before (A) and after biotransformation (B);

FIGS. 2(A) and (B) show the inhibitory effect of PPE and docetaxel on tumor growth of heterotopic subcutaneous tumor-bearing BALB/c nude mice. H441-luc were subcutaneously injected into the mice at a concentration of $1.2 \times 10^6$ cells/100 µL PBS. PPE treatments (two dosages 100 mg/mL b.w. and 200 mg/mL b.w.) once every two days by intraperitoneal injection into tumor-bearing animals over a period of 5 weeks. (A) Bioluminescence imaging of mice shown over the period of 5 weeks. (B) Bar graphs are quantified by Living Image analysis software (n=8-10). Data were analyzed by Student's t-test and are shown as mean±SD. *$P<0.05$ compare with control. § † $P<0.05$ compared with tumor group.

FIGS. 3(A) and (B) show the inhibitory effect of PPE on tumor growth of orthotropic lung tumor-bearing BALB/c nude mice. H441-luc were orthotopically injected into the lung of mice at a concentration of $0.8 \times 10^6$ cells/70 µL PBS. PPE treatments (three dosages 25, 50, and 100 mg/mL b.w.) twice a week by intraperitoneal injection into tumor-bearing animals over a period of 4 weeks. (A) Representative non-invasive bioluminescence images show tumor progression of mice in orthtopic model. (B) Bar graphs were quantified by Living Image analysis software (n=8-10). Data were analyzed by Student's t-test and are shown as mean±SD*$P<0.05$ compared with control. § $P<0.05$ compared with week 4 tumor group;

FIGS. 5(A) and (B) show the inhibitory effects of PPE on analysis of tumor volume in orthotopic model. (A) The micro-CT images and quantitative end-points for lung tumor growth. Longitudinal and transverse micro-CT images of tumor growth in control and treatment of PPE. Each tumor scanned by micro-CT was reconstructed to three-dimensional images (axial, sagittal, and coronal), and diameters measured periodically as indicated. Data represent presence of tumor value in each group. (B) The tissue of lung lesions in nude mice. Representative lung tumor formed in different group. Tumors observed in the lungs are indicated with a yellow arrow;

FIGS. 7(A) and (B) show the inhibitory effects of PPE on human lung adenocarcinoma cell lines. The human lung adenocarcinoma cells H441 and A549 treated with different doses of PPE (21.5-345 μg/mL) for 24 H and 48 H. (A) H441 and (B) A549 were quantified by MTT assay and the number represents percent of cell viability. The values represent the means±SD of three independent experiments. When # $P<0.05$ and *$P<0.001$ it is considered significant compared with control.

DETAILED DESCRIPTION OF THE INVENTION

The invention provides a fermented *Pennisetum* extract, which has an advantageous effect in treating and preventing a cancer without toxicity to normal cells.

In this specification and the appended claims, the singular forms "a," "an," and "the" include plural reference unless the context clearly dictates otherwise. Unless defined otherwise, all technical and scientific terms used herein have the meaning commonly understood by a person skilled in the art to which this invention belongs.

As used herein, the term "cancer" denotes a disease, condition, trait, genotype or phenotype characterized by unregulated cell growth or replication as is known in the art.

As used herein, the terms "prevent," "preventing" and "prevention" in the context of the administration of a therapy to a subject refer to the prevention or inhibition of the recurrence, onset, and/or development of a cancer.

As used herein the term "treat" or treatment" refers to reducing or alleviating at least one adverse clinical symptom associated with cancer.

As used herein, the term "a therapeutically effective amount" refers to an amount sufficient to achieve the intended purpose of treating cancer.

In another aspect, the invention provides a process for preparing a fermented *Pennisetum* extract, comprising the following steps: (a) culturing *Pennisetum* solution with *Aspergillus niger* for a biotransformation; (b) collecting the resulting cultured solution and then extracting the extract with an organic solvent; and (c) analyzing the extract by High Performance Liquid Chromatography (HPLC) at 330 nm.

Accordingly, the invention provides a fermented *Pennisetum* extract prepared by the process of the invention. In one aspect, the invention provides a fermented *Pennisetum* extract prepared by the process comprising the following steps: (a) culturing *Pennisetum* solution with *Aspergillus niger* for a biotransformation; (b) collecting the solution and then extracting the extract with an organic solvent; and (c) analyzing the extract by High Performance Liquid Chromatography (HPLC) at 330 nm.

In one embodiment, the *Pennisetum* solution is 40% (v/v) *Pennisetum alopecuroides* (L.) in ethanol.

In one embodiment, the organic solvent of step (b) is an alcohol. Preferably, the alcohol is methanol, ethanol, propanol or isopropanol.

In one embodiment, after step (b), the process comprises a further step (b1) of concentrating the extract to a concentrated extract can be performed.

In one embodiment, the HPLC is carried out under the following condition: the mobile phase is 0.5 mM ammonium acetate solution with formic acid adjusted pH to 3.5 (solvent A)-methanol (solvent B) in the following gradient:

| Time (min) | flow | A(%) | B(%) |
| --- | --- | --- | --- |
| 0 | 1.0 | 70 | 30 |
| 8 | 1.0 | 60 | 40 |
| 13 | 1.0 | 50 | 50 |
| 20 | 1.0 | 60 | 40 |
| 25 | 1.0 | 70 | 30 |

In a further embodiment, the HPLC is detected at 331 nmYMC-Triart C18 column (5 um×250 mm×4.6 mmI.D.) by Hewlett Packard HP-1100 system.

The above-mentioned HPLC assay can obtain specific components. Accordingly, the invention provides a fermented *Pennisetum* extract, comprising a compound ZG5236 having a chromatograph having at least a peak at retention times of 17.18 to 17.98 minutes. Preferably, the peak is at retention time of about 17.53 minutes in the HPLC. In a further embodiment, the extract comprises a compound ZG5235 having a chromatograph having the peak at retention times of: 16.20 to 17.10 minutes, preferably, 16.63 minutes; and/or a compound ZG5237 having a chromatograph having the peak at retention times of: 19.00 to 19.36 minutes, preferably, 19.18 minutes. In one embodiment, the fermented *Pennisetum* extract comprises compounds ZG5235, ZG5236 and ZG5237. In another embodiment, the amount of ZG5236 after biotransformation is higher than that before the transformation, while the amounts of ZG5235 and ZG5237 after biotransformation are lower than those before the transformation. Preferably, the amount of ZG5236 after biotransformation increases about 20.99% in comparison with that before biotransformation. The amounts of ZG5235 and ZG5237 after biotransformation reduce about 8.8% and about 1.39%, respectively.

In one embodiments, ZG5236 accounts for 5.88% of the extract. In another embodiment, the amounts of ZG5235 and ZG5237 account for 1.47% and 0.13%, respectively.

In some embodiments, the *Pennisetum* mentioned herein is selected from the group consisting of: *Pennisetum alopecuroides* (L.), *Pennisetum clandestinum*, *Pennisetum polystachion* (L.), *Pennisetum purpureum* and *Pennisetum setosum*. Preferably, the *Pennisetum* is *Pennisetum alopecuroides* (L.) or *Pennisetum purpureum*.

In another aspect, the present invention provides a composition comprising the fermented *Pennisetum* extract. The fermented *Pennisetum* extract can be suitably formulated and introduced into a subject or the environment of the cell by any means recognized for such delivery. Such compositions typically include the agent and a pharmaceutically or a food-acceptable carrier. As used herein, the language "pharmaceutically acceptable carrier" or "food-acceptable carrier" includes saline, solvents, dispersion media, coatings, antibacterial and antifungal agents, isotonic and absorption delaying agents, and the like, compatible with administration. Preferably, the composition is a pharmaceutical composition, dietary supplement composition, a supplementary composition for a patient receiving chemotherapy, health food composition or food composition.

A composition is formulated to be compatible with its intended route of administration. Examples of routes of administration include parenteral, e.g., intravenous, intradermal, subcutaneous, oral, transdermal, topical, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

Compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), or a suitable mixture thereof.

Oral compositions generally include an inert diluent or an edible carrier. For the purpose of oral administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferably, the composition is in the form of solution, suspension, emulsion, powder, pill, tablet or capsule.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

The composition can further comprise a second anti-cancer agent. The second anti-cancer agent includes, but is not limited to, an alkylating agent, an antimetabolite, an anti-microtubule agent, a topoisomerase inhibitor or a cytotoxic antibiotic. Preferably, the second anti-cancer agent is cisplatin, taxol, docetaxel, vinorelbine, vindesine, vinflunine, gemcitabine, methotrexate, gefitinib, lapatinib or erlotinib.

In another aspect, the invention provides a method for treating or preventing a cancer and/or invasion and metastasis of cancer in a subject in need thereof, comprising administering to the subject an effective amount of a fermented *Pennisetum* extract of the invention.

In one embodiment, the *Pennisetum* extract is administered in combination with radiotherapy and chemotherapy. In another embodiment, the method comprises further administering a second anti-cancer agent. The *Pennisetum* extract and the second anti-cancer agent are administered simultaneously, sequentially or separately.

The cancer, cancer invasion or cancer metastasis to be treated or prevented is lung cancer, squamous cell carcinomas of the lung, head and neck, breast cancer, ovarian cancer, prostate cancer, gastric carcinoma, cervical cancer, esophageal carcinoma, bladder cancer, brain cancer, liver cancer, or colon cancer. Preferably, the cancer is lung cancer. More preferably, the lung cancer is small cell lung cancer or non-small cell lung cancer.

Dosage of one or more agents of the invention (e.g., epigenetic modulating agents and/or immune modulating agents) can be determined by one of skill in the art and can also be adjusted by the individual physician in the event of any complication. Typically, the dosage ranges from 50 mg/kg body weight to 100 mg/kg body weight.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

EXAMPLES

Example 1 Preparation of a Fermented *Pennisetum alopecuroides* (L.) Extract

*Aspergillus niger* was inoculated and incubated at 27° C. for 2 days. Erlenmeyer flasks (250 mL) containing 30 mL of culture medium were inoculated with cells before 4 days of subculture. The cultures were incubated with shaking speed of 200 r/min at 27° C. for 2 days. After that, the culture broth was centrifuged (10,000 g) at 4° C. for 20 min, and the cultured cells were washed with sterilized water three times, collected and stored at 4° C. for the following use.

The suspended cells were cultivated in a 250 mL flask containing 30 mL liquid transformation broth (seed medium, initial pH 5.5-6). For preparative biotransformation, 2 ml of prepared substrate of 40% (v/v) *Pennisetum alopecuroides* (L.) solution was dissolved in 50% (v/v) ethanol. The resulting solution was added to one flask with resting cell cultures, and one additional flask without substrate was taken as the control. After an additional 5 days of incubation at 30° C. with shaking speed of 160 rpm, the cell cultures were filtrated to collect the broth. The resulting broth was extracted two times by equivalent volume of methanol, and all the extracted solutions were concentrated in vacuum at 60° C. Residues were dissolved in methanol and analyzed by HPLC.

The crude samples with two-step purification were analyzed by preparative separation. The RP-HPLC system used Waters 996 photodiode array detector. The column used was a reversed-phase YMC-triate C18 column. The mobile phase was filtered, degassed by sonication and pumped through the system at flow rate of 1.0 ml/min, peak detection performed at 254 and 330 nm. The mobile phase was 0.5 mM ammonium acetate solution with formic acid adjusted pH to 3.5 (solvent A)-methanol (solvent B) in the gradient mode as follows:

TABLE 1

Gradient elution program employed for RP-HPLC separation of the fermented Pennisetum alopecuroides (L.) extract

| Time | Solvent (A) | Solvent(B) |
|---|---|---|
| 0 | 70 | 30 |
| 12 | 60 | 40 |
| 17 | 50 | 50 |
| 22 | 60 | 40 |
| 26 | 65 | 35 |
| 30 | 70 | 30 |

Figure 1:
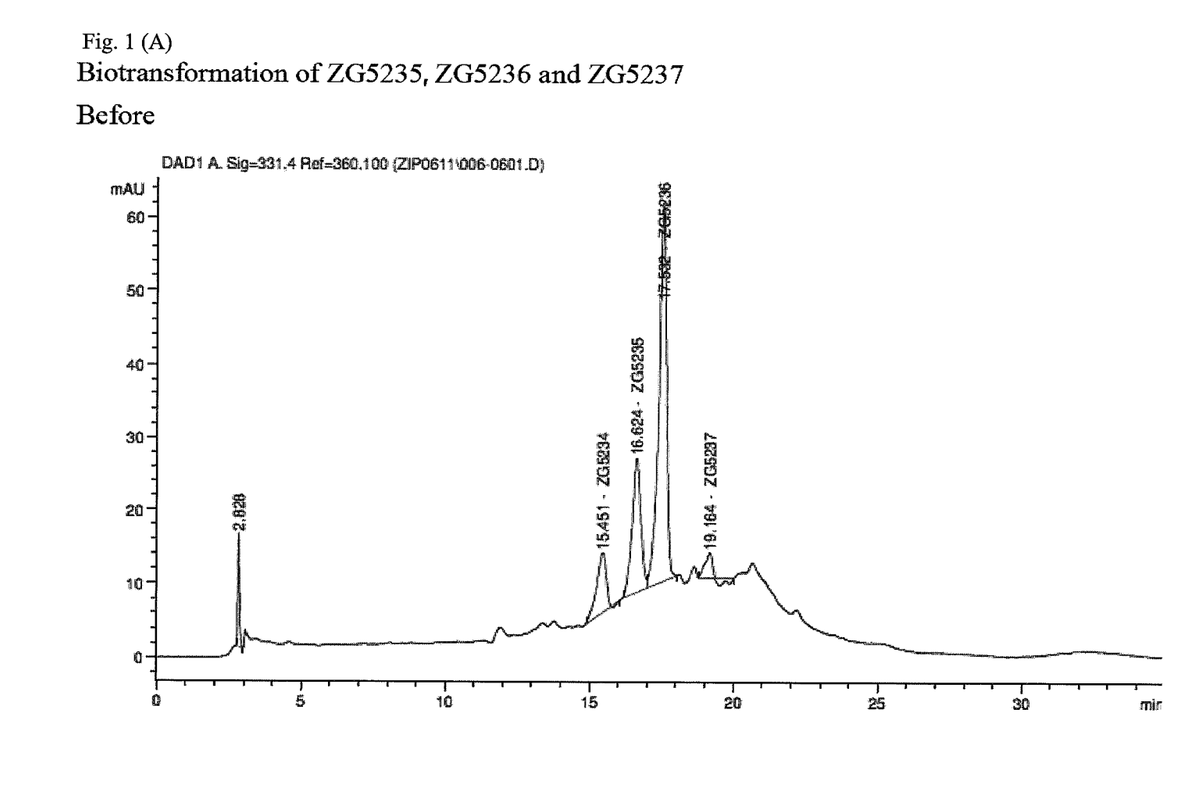

The HPLC spectra of Pennisetum alopecuroides (L.) solution before and after biotransformation are shown in FIG. 1. The biotransformation rate thereof is shown in Table 1.

TABLE 1

The Change of Biotransformation with each Compounds on HPLC chromatograph Area (%)

| Treatment | Solvent Peak | ZG5234 | ZG5235 ZG5236 | | ZG5237 |
|---|---|---|---|---|---|
| Before transformation | 3.81 | 11.15 | 23.56 | 58.80 | 2.68 |
| After transformation | 4.15 | — | 14.76 | 79.79 | 1.29 |
| Difference % between after transformation and before trandformation | 0.34 | −11.15 | −8.8 | +20.99 | −1.39 |

Example 2 Tumor Growth Assay in Heterotopic Animal Model

Male BALB/c nu/nu mice were used in the heterotopic model and divided into four groups, control group (5 mice), tumor group (8 mice) and two experimental groups (100-PPE group and 200-PPE group). The mice of the control group and the tumor group were subjected to intraperitoneal injection (i.p.) with vehicle, while 6 mice of the experimental group, 100-PPE group, were i.p. administered with 100 mg/kg of the fermented Pennisetum alopecuroides (L.) extract (PPE) obtained in Example 1 and 6 mice of the experimental group, 200-PPE group, were administered with 200 mg/kg of the fermented Pennisetum alopecuroides (L.) extract obtained in Example 1.

Figure 2:
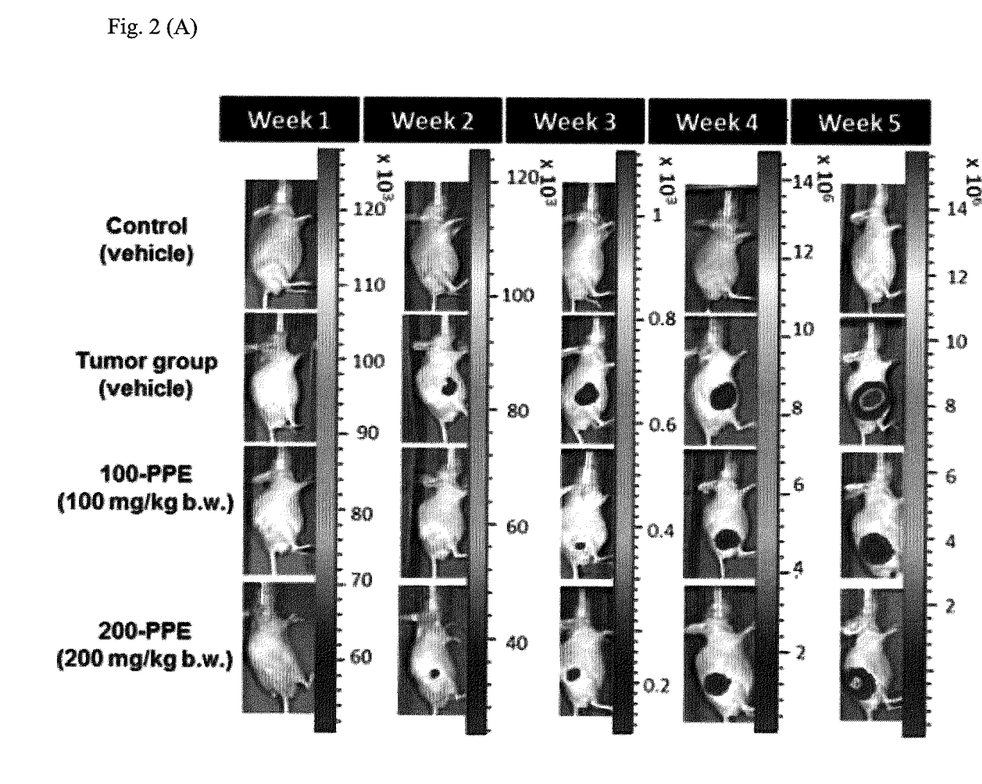

After PPE was administered for one week, the cell solution of human lung adenocarcinoma cell line, NCl-H441, in matrigel was subcutaneously injected to the back of the mice ($1.2 \times 10^6$ cells/100 μL/mice) once every two days. The tumor growth was monitored by Non Invasion In Vivo Imaging System (IVIS). FIG. 2 shows that the average tumor sizes in the 100-PPE group ($1.42+/-0.78 \times 10^8$ photons/sec) and the 200-PPE group ($2.17+/-0.54 \times 10^8$ photons/sec) from the fourth week are significantly smaller than those of the tumor group. The results show that PPE can significantly inhibit tumor growth, by 77%.

Example 3 Tumor Growth Assay in Orthotopic Model

Male BALB/c nu/nu mice were used in the orthotopic model and divided into five groups, control group (5 mice), tumor group (10 mice), three experimental groups (25-PPE, 50-PPE and 100-PPE) (each group for 10 mice) and docetaxel group (8 mice). The mice of the control group and the tumor group were subjected to intraperitoneal injection (i.p.) with vehicle, while 10 mice of each of the experimental groups, 25-PPE group (25 mg/kg of PPE), 50-PPE group (50 mg/kg of PPE) and 100-PPE group (100 mg/kg of PPE), were i.p. administered with 25 mg/kg of PPE, 50 mg/kg of PPE and 100 mg/kg of PPE obtained in Example 1, respectively, and 8 mice of the docetaxel group were administered with 2.5 mg/kg of docetaxel.

Figure 3:
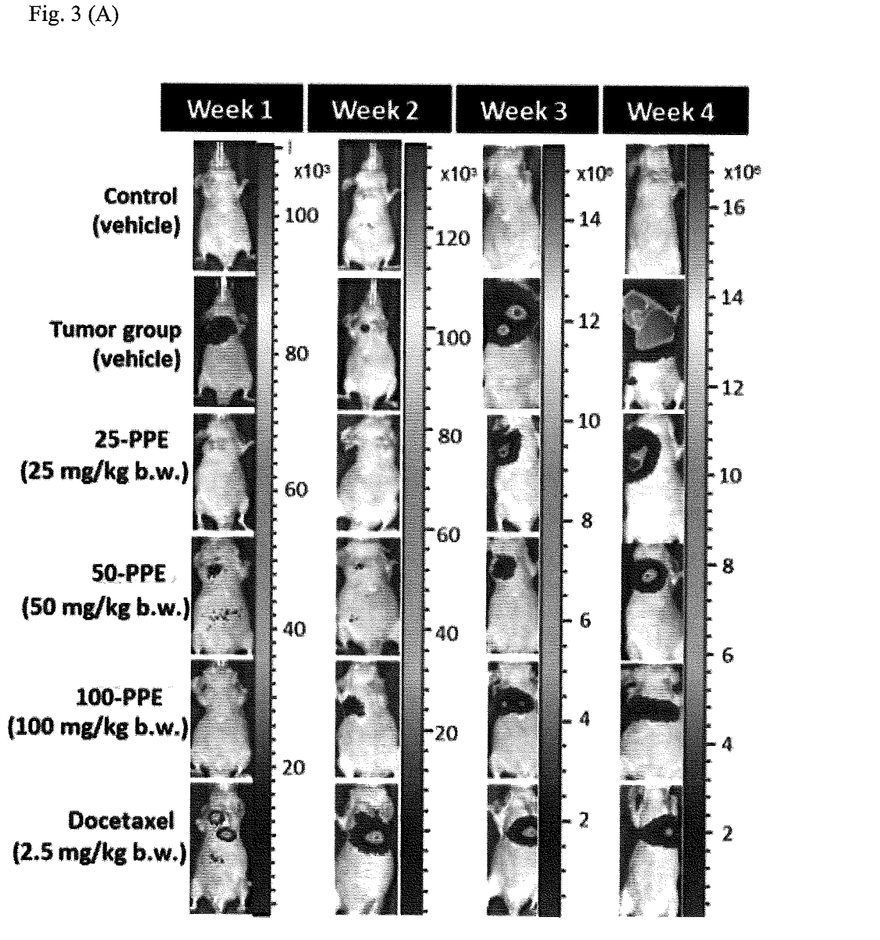
Figure 4:
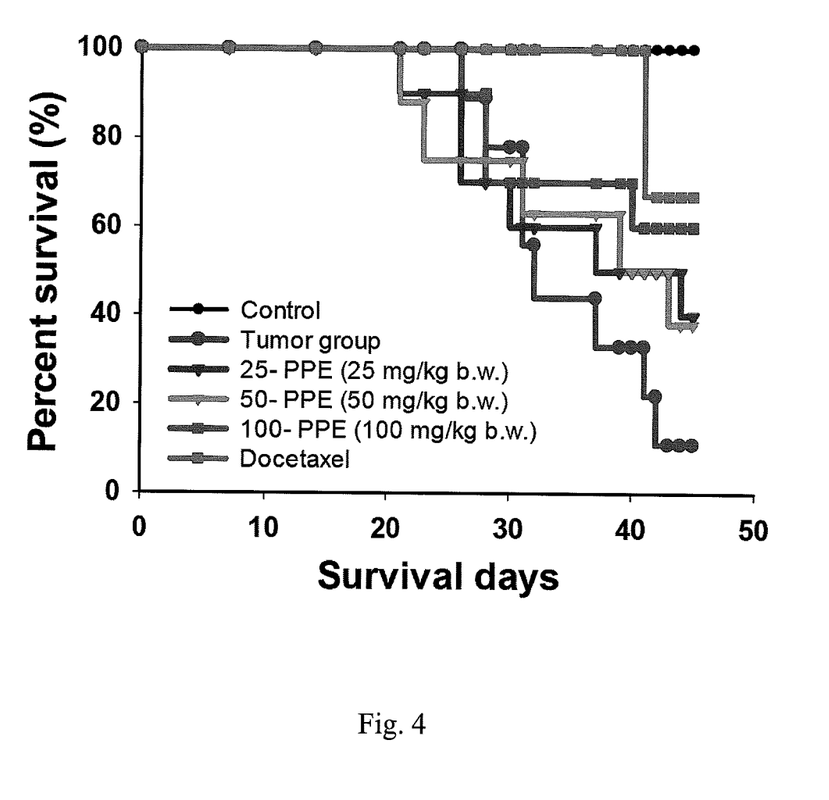
FIG. 4 shows PPE increased survival in orthotopic lung tumor-bearing BALB/c nude mice. Kaplan-Meier cumulative survival analysis revealed a significant ($p<0.05$) increase in lifespan of PPE with different dosages (25, 50, and 100 mg/kg b.w.) and docetaxel (2.5 mg/kg b.w.) extended nude mice survival (n=8-10 in every group)

The mice were injected with the cell solution of human lung adenocarcinoma cell line, NCl-H441, in matrigel ($0.8 \times 10^6$ cells/70 μL/mice). Three days after injections, the PPEs at the above-mentioned doses were i.p. administered to the mice twice every two weeks. The tumor growth was monitored by Non Invasion In Vivo Imaging System (IVIS). FIG. 3 shows that the tumor volumes in the 100-PPE group ($3.2+/-2.7 \times 10^7$ photons/sec), the 50-PPE group ($2.6+/-0.07 \times 10^7$ photons/sec), the 25-PPE group ($3.5+/-2.9 \times 10^7$ photons/sec) and the docetaxel group ($0.5+/-0.07 \times 10^7$ photons/sec) from the fourth week are significantly smaller than those of the tumor group ($7.6+/-1.8 \times 10^8$ photons/sec). The results show that PPE at the doses from 25 mg/mL to 100 mg/mL can significantly inhibit tumor growth in the orthotopic model. The animal survival rate (60%) of the 100-PPE group is significantly higher than that of the tumor group (11%) (see FIG. 4).

Example 4 Computed Tomography (CT) Lung Screening Assay

Figure 5:
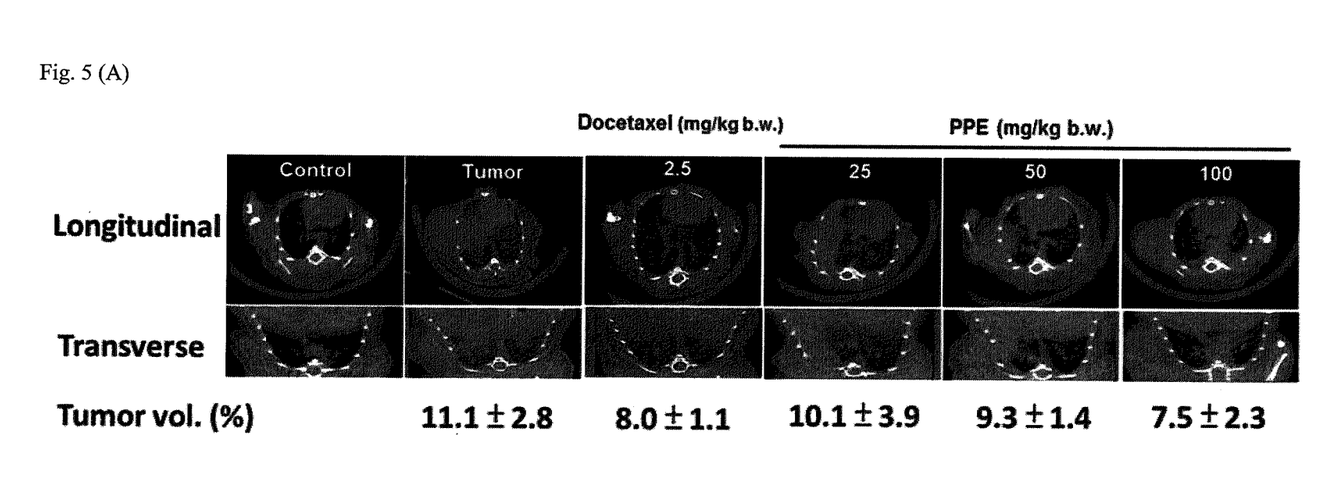

In the orthotopic model of Example 3, the mice were subjected to CT lung screening to detect the tumor size in lung at the fourth week. The tumor accounts for 11.1+/−2.8% of the lung in the tumor group, 10.1+/−3.9% in the 25-PPE group, 9.3+/−1.4% in the 50-PPE group, 7.5+/−2.3% in the 100-PPE group and 8.0+/−1.1% in the docetaxel group (see FIG. 5). The results show that the tumor group has the highest tumor volume ratio and a 32% reduction of the tumor volume ratio can be achieved in the 100-PPE group. FIG. 5(B) shows that significant reductions in tumor growth and lung nodules (see white arrows) are possible in the 100-PPE group.

Example 5 H&W Stain of Lung Histology Assay

Figure 6:
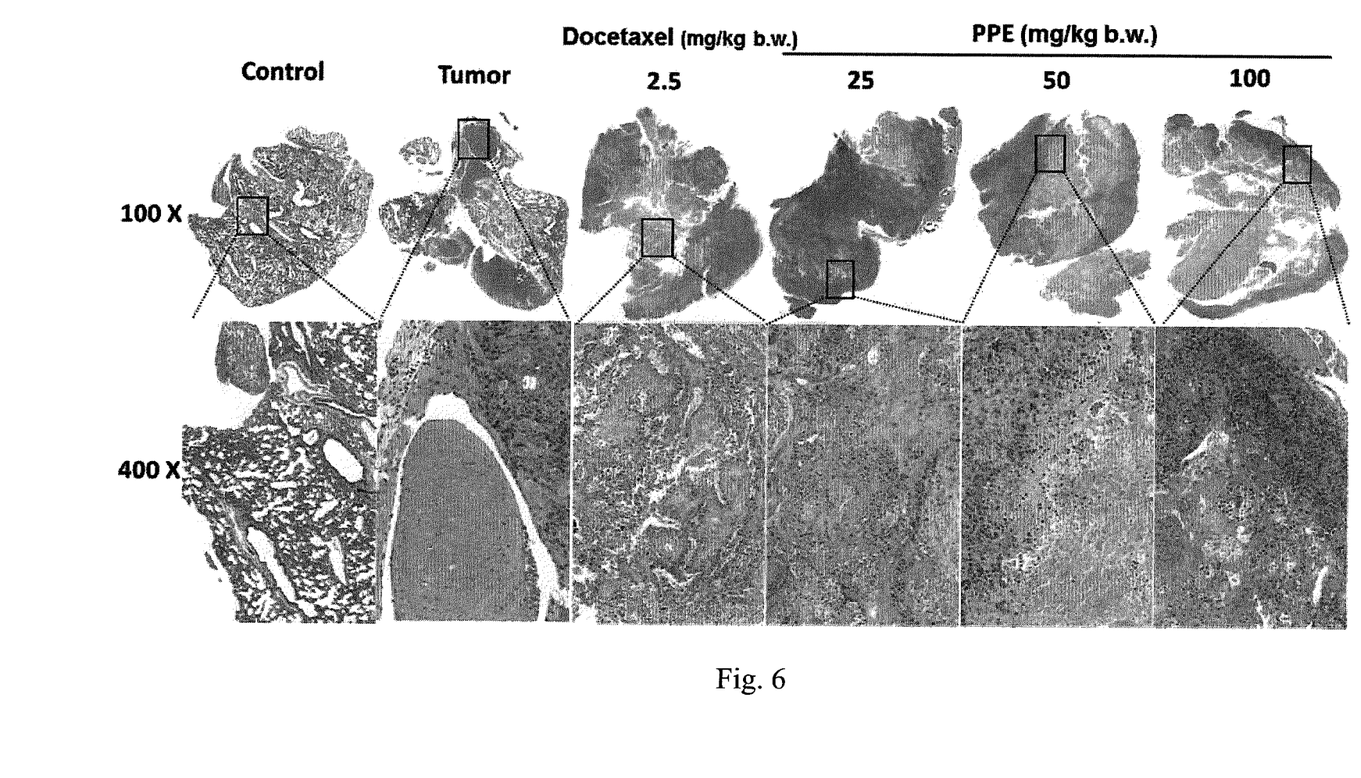
FIG. 6 shows the effect of PPE on histopathological analysis of primary lungs at 4 weeks of age in orthtopic BALB/c mice. Lung tumor was induced by injection of H441/luc cells (0.8×106 cells/80 μL) (H&E stain, 100× and 400×). Mice were treated with varied doses of PPE (25, 50, 100 mg/kg) and docetaxel (2.5 mg/kg b.w.)

Hematoxylin and eosin (H&E) stains were used to observe the tumor tissues in the mice. As shown in FIG. 6, there is no cell proliferation in the lung tissues in the control group, whereas the cells in the tumor groups show light color in cytoplasm and the nuclei of the cells are enlarged and folded, and the tumor cells show excessive proliferation in the tumor group; and the 25-PPE, 50-PPE and 100-PPE groups show no stains in the nuclei. The results show that the PPEs can induce tumor apoptosis.

Example 6 Selective Toxicity of PPEs on Tumor Cells

Figure 7:
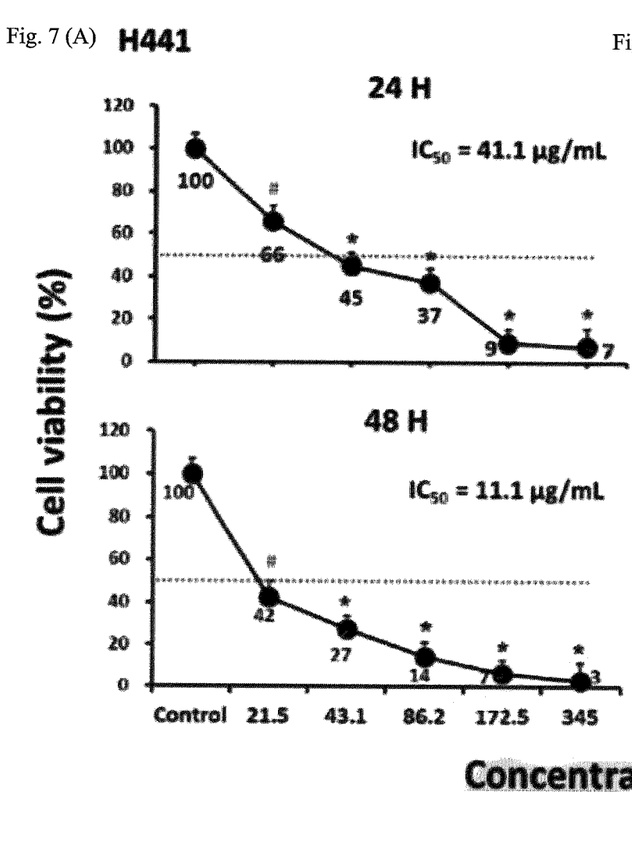
Figure 8:
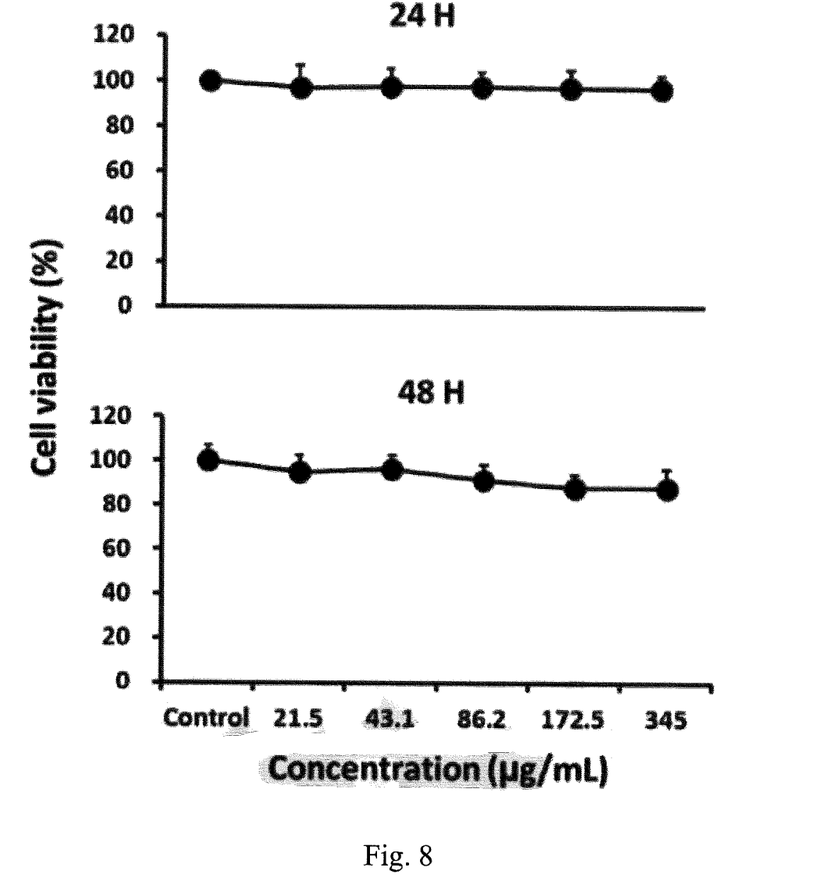
FIG. 8 shows the effects of PPE on normal human cell line. The human uterine smooth muscle cell (UTSMC) treated with different doses of PPE (21.5-345 μg/mL) for 24 H and 48 H. There is no cytotoxicity in UTSMC cell at 24 H and 48 H. The values represent the means±SD of three independent experiments. There is no statistical difference in different treatments of PPE.

MTT (3-(4,5-Dimethylthiazol-2-yl)-2,5-diphenyltetrazolium bromide) assay was used to determine the cell survival rate. A549 cells (adenocarcinomic human alveolar basal epithelial cells) and H441 cells were seeded in a 96-well plate (3000 cells/well) and cultured at 37° C. After 24 hours, PPEs at different concentrations (21.5 µg/mL to 345 µg/mL) were added to the plate for culture. The solutions were taken from the wells at 24 hours and 48 hours and then subjected to MTT assay. The $IC_{50}$ values of the H441 cells were 41.1 µg/mL and 11.1 µg/mL at 24 hours and 48 hours (FIG. 17(A)). The $IC_{50}$ values of the A549 cells were 67.7 µg/mL and 61.1 µg/mL at 24 hours and 48 hours (FIG. 17(B)). PPEs at different concentrations (21.5 µg/mL to 345 µg/mL) had no toxicity on normal uterine smooth muscle cells after culturing 24 hours and 48 hours (FIG. 8). The results show that PPEs have selective toxicity on tumor cells, while there is no toxicity on normal cells.

The invention claimed is:

1. A fermented *Pennisetum alopecuroides* extract, comprising about 5.88% of a compound ZG5236 giving rise to a chromatograph having at least a peak at retention times of 17.18 to 17.98 minutes assayed by HPLC, wherein the extract comprising said compound is capable of reducing tumor growth in a human.

2. The extract of claim 1, wherein the peak is at retention time of about 17.53 minutes.

3. The extract of claim 1, which further comprises a compound ZG5235 giving rise to a chromatograph having the peak at retention times of 16.20 to 17.10 minutes, and/or a compound ZG5237 giving rise to a chromatograph having the peak at retention times of 19.00 to 19.36 minutes.

4. The extract of claim 3, wherein the peak of ZG5235 is at a retention time of about 16.63 minutes and the peak of ZG5237 is at a retention time of about 19.18 minutes.

5. The extract of claim 3, wherein ZG5235 and ZG5237 are present in percent amounts of 1.47% and 0.13% of the extract, respectively.

6. The extract of claim 1, which is prepared by the process comprising the following steps: (a) culturing a *Pennisetum alopecuroides* solution with *Aspergillus niger* for biotransformation; (b) collecting the solution and then extracting an extract with an organic solvent; and (c) analyzing the extract by High Performance Liquid Chromatography (HPLC) at 330 nm.

7. The extract of claim 6, wherein the amount of ZG5236 after the biotransformation increases about 20.99% in comparison with that before the biotransformation, or the amounts of ZG5235 and ZG5237 after the biotransformation reduce about 8.8% and about 1.39%, respectively.

8. The extract of claim 6, wherein the organic solvent of step (b) is an alcohol.

9. The extract of claim 8, wherein the alcohol is methanol, ethanol, propanol or isopropanol.

10. The extract of claim 6, wherein after step (b), the process comprises a further step (b1) of concentrating the extract to a concentrated extract.

11. The extract of claim 6, wherein the HPLC is carried out under the following condition: the mobile phase is 0.5 mM ammonium acetate solution with formic acid adjusted pH to 3.5 (solvent A)-methanol (solvent B) in the following gradient:

| Time | Solvent (A) | Solvent(B) |
|------|-------------|------------|
| 0    | 70          | 30         |
| 12   | 60          | 40         |
| 17   | 50          | 50         |
| 22   | 60          | 40         |
| 26   | 65          | 35         |
| 30   | 70          | 30         |

12. A process for preparing a fermented *Pennisetum* extract of claim 1, comprising the following steps: (a) culturing *Pennisetum* solution with *Aspergillus niger* for a biotransformation; (b) collecting the resulting cultured solution and then extracting the solution with an organic solvent to obtain an extract; and (c) analyzing the extract by High Performance Liquid Chromatography (HPLC) at 254 nm and 330 nm.

13. A composition comprising an effective amount of the *Pennisetum alopecuroides* extract of claim 1 and a second anti-cancer agent.

14. The composition of claim 13, wherein the second anti-cancer agent is an alkylating agent, an antimetabolite, an anti-microtubule agent, a topoisomerase inhibitor or a cytotoxic antibiotic.

15. The composition of claim 14, which is a pharmaceutical composition, dietary supplement composition, a supplementary composition for a patient receiving chemotherapy, a health food composition or a food composition.

16. The composition of claim 15, which is in the form of solution, suspension, emulsion, powder, pill, tablet or capsule.

* * * * *